US009332697B2

(12) United States Patent
Van Dun et al.

(10) Patent No.: US 9,332,697 B2
(45) Date of Patent: *May 10, 2016

(54) NEAR REVERSE BREEDING

(75) Inventors: Cornelis Maria Petrus Van Dun, Roosendaal (NL); Robert Helene Ghislain Dirks, Oudenbosch (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 1424 days.

This patent is subject to a terminal disclaimer.

(21) Appl. No.: 11/848,828

(22) Filed: Aug. 31, 2007

(65) Prior Publication Data
US 2008/0098496 A1    Apr. 24, 2008

Related U.S. Application Data

(63) Continuation-in-part of application No. PCT/EP2006/002095, filed on Mar. 2, 2006.

(30) Foreign Application Priority Data

Mar. 3, 2005 (EP) .................................. 05075519
Jan. 5, 2006 (EP) .................................. 06075024

(51) Int. Cl.
*A01H 1/00* (2006.01)
*A01H 1/02* (2006.01)
*A01H 4/00* (2006.01)
*C12N 15/82* (2006.01)

(52) U.S. Cl.
CPC .. *A01H 1/02* (2013.01); *A01H 1/00* (2013.01); *A01H 4/008* (2013.01); *C12N 15/8218* (2013.01)

(58) Field of Classification Search
USPC .......................................... 800/260, 271, 295
See application file for complete search history.

(56) References Cited

U.S. PATENT DOCUMENTS 4,731,499 A * 3/1988 Puskaric et al. ........... 800/320.1
6,693,232 B1 * 2/2004 Bergemann ................ 800/320.1

FOREIGN PATENT DOCUMENTS

| WO | WO 97/43427 | 11/1997 |
|---|---|---|
| WO | WO 99/32661 | 7/1999 |
| WO | WO 00/24914 | 5/2000 |
| WO | WO 01/32001 | 5/2001 |
| WO | WO 03/017753 | 3/2003 |
| WO | WO 03017753 A2 * | 3/2003 |
| WO | WO 2005/014858 | 2/2005 |
| WO | WO 2006/094774 | 9/2006 |

OTHER PUBLICATIONS

Zhang et al. J Horticultural Sci & Biotech 78: 84-88, 2002.*
Ramanna et al (2003) Euphytica (2003) 133: 3-18.*
J. A. Buso, et al., Chromosome Regions Between Centromeres and Proximal Crossovers Are The Physical Sites of Major Effect Loci for Yield in Potato: Generic Analysis Employing Meiotic Mutants, PNAS (1999) vol. 96, p. 1773-1778.
Peter J. van Dijk, et al., Formation of Unreduced Megaspores (Diplospory) in Apomictic Dandelions (Taraxacum officinale, s.l.) is Controlled by a Sex-Specific Dominant Locus, Genetics (2004) vol. 166, p. 483-492.
Jaap M. van Tuyl, et al., Identification of 2n-Pollen Producing Interspecific Hybrids of Lilium Using Flow Cytometry, Cytologia (1989) vol. 54, p. 737-745.
Xin-Zhong Zhang, et al., Creating Triploid Germplasm Via Induced 2n Pollen in Capsicum Annuum L., Journal of Horticultural Science & Biotechnology (2002) vol. 78 No. 1, p. 84-88.
Ramanna, M.S., et al., "Relevance of sexual polyploidization for crop improvement—A review," Euphytica 133: 3-18, 2003.
Okazaki, Keiichi, et al., "Induction of 2n pollen in tulips by arresting the meiotic process with nitrous oxide gas," Euphytica (2005) 143: 101-114.
Peloquin, Stanley J., et al., "Perspectives; Anecdotal, Historical and Critical Commentaries on Genetics," Genetics 153: 1493-1499 (Dec. 1999).
Lim, Ki-Byung, et al., Occurrence of SDR 2N-gametes in *Lilium* Hybrids, Breeding Science 54: 13-18 (2004).
Lelivelt, Cilia CLC, et al., Poster: Emerging technologies, Abs #907: Reverse breeding: a novel plant breeding concept, American Society of Plant Biologists 2004.
Werner, Joanna E. et al., "Use of half-tetrad analysis to discriminate between two types of 2n egg formation in a potato haploid," Genome, 35: 741-745, 1992.
Bretagnolle, F., et al., Tansley Review No. 78; Gametes with the somatic chromosome No. mechanisms of their formation and role in the evolution of autopolyploid plants, XP-002381901, Aug. 18, 1994.
Murthy, T.G.K., et al., "Second Division Restitution in a Fertile Interspecific Triploid Hybrid of Groundnut," Cytologia 52: 667-670, 1987.
Dirks, Rob, et al., "Reverse breeding: a novel breeding approach based on engineered meiosis," Plant Biotechnology Journal (2009) 7, pp. 837-845.
Rotarenco, VA Production of matroclinous maize haploids following natural and artificial pollination with a haploid inducer, MaizeGDB, vol. 76, 2002.

* cited by examiner

*Primary Examiner* — David T Fox
*Assistant Examiner* — Jared Shapiro
(74) *Attorney, Agent, or Firm* — Vedder Price P.C.; Thomas J. Kowalski; Deborah L. Lu

(57) ABSTRACT

Provided is a method for producing a homozygous non-human organism from a heterozygous non-human organism, which homozygous organism can be crossed to obtain a hybrid, comprising providing a heterozygous starting organism; allowing the organism to produce SDR-0 cells through meiosis, which cells originate from second division restitution; regenerating SDR-0 organisms from the SDR-0 cells; and producing the homozygous organism from the SDR-0 organisms thus obtained. Further provided is a method for producing a hybrid, comprising crossing a first homozygous organism that is produced according to the above method with a second homozygous organism. Also provided is a homozygous non-human organism and hybrid non-human organisms obtainable by these methods. In a preferred embodiment, the organisms are plants.

17 Claims, 13 Drawing Sheets

Meiosis

Parent A    X    Parent B

Hybrid AB

Meiosis 1: chromosome doubling

Meiosis 1: recombination took place

● = centromere

Meiosis 2: formation of spores/gametes

Groups of recombined/parental chromosomes 3 possible examples of spores/gametes

Corresponding "Doubled Haploids"

Second division does not take place = second division restitution 4 examples of spores/gametes (SDR-0):
note the partial heterozygocity (1)  (2)  (3)

(4)

Note that in the 3th and 4th example the basic make up of the chromosome sets are derived
from the respective parents; such sets resemble "BIL's" but in heterozygous state.
Examples 1 and 2 resemble "RIL's" in a heterozyous state.

Meiosis 1: chromosome doubling

Meiosis 1: recombination took place

Possible gametes from 1 recombination event
from 1 SDR event

Doubled haploid (left) form a specific spore/gamete from an SDR-0 event resembling one of the original parental lines (right).

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acctccgaga actccgttaa g                                             21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 2
tgcctgcttt ctaccacttc                                                      20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttctcaagtg gcaaggtgtc                                                      20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atccctcttt ggtggagtag                                                      20
```

NEAR REVERSE BREEDING

CROSS-REFERENCE TO RELATED APPLICATIONS

This application is a continuation-in-part of International application no. PCT/EP2006/002095, filed Mar. 2, 2006, published as WO 2006/094773 on Sep. 14, 2006, and claiming priority to EP 05075519.8, filed Mar. 3, 2005 and EP 06075024.7, filed Jan. 5, 2006.

All of the foregoing applications, as well as all documents cited in the foregoing applications ("application documents") and all documents cited or referenced in the application documents are incorporated herein by reference. Also, all documents cited in this application ("herein-cited documents") and all documents cited or referenced in herein-cited documents are incorporated herein by reference. In addition, any manufacturer's instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

FIELD OF THE INVENTION

The present invention relates to a method for producing a homozygous non-human organism from a heterozygous non-human organism, which homozygous organism can be crossed to obtain a hybrid. The invention relates in particular to plants.

BACKGROUND OF THE INVENTION

Plant breeding is one of the fundamental occupations of mankind that is of pivotal importance for providing domesticated species that feed the world. Plant breeding is by consequence old and was originally based on selecting and propagating those plants that were outperforming in local selection fields.

Contemporary plant breeding is highly depending on knowledge of genetics and technologically supported by methods such as doubled haploids (DH) (see fi. Haploids in Crop Improvement II eds; Palmer C, Keller W, and Kasha K (2005) in: Biotechnology in Agriculture and Forestry 56 Eds; Nagata T, Lörz H, and Widholm J. Springer-Verlag Berlin Heidelberg N.Y., ISBN 3-500-22224-3) and molecular markers (see fi. De Vienne ed. (2003) Molecular Markers in Plant Genetics and Biotechnology. Science publishers Inc. Enfield, N.H. USA. ISBN 1-57808-239-0).

Genetic mechanisms during sexual reproduction have evolved to increase genetic variation which enhances the chances of survival of a species in a changing environment. Meiotic recombination, independent chromosome assortment and the mating system are main contributing factors in this respect. However, in plant breeding these mechanisms may act counterproductive especially in those cases when genetically heterozygous plants have been identified with high agronomic or horticultural value. Redistribution of genetic factors results in the generation of genetically dissimilar and therefore heterogeneous plants and by consequence loss of commercially desirable traits.

In order to counter this effect, a number of technologies is available to the plant breeder. One possibility is to propagate plants vegetatively which leads to a complete preservation of their genetic composition as multiplication occurs exclusively through mitosis. For many plant species, in vitro tissue culture is being used to vegetatively propagate plants although other methods like producing cuttings in vivo may be applicable as well.

A disadvantage of vegetative propagation when compared to propagation through seeds is the fact that it is labour intensive and thereby costly. Furthermore, it is difficult to store plants for longer periods of time posing logistic problems and the risks of infections of the plant material with pathogens, like viruses, is considerably larger as compared to a situation in which plant material is propagated through seeds.

As an alternative, vegetative propagation may be achieved through the formation of asexual seeds, which is generally referred to as apomixis. Apomixis which occurs naturally in a number of species may be induced in sexually propagating plant species by genetic engineering. Currently, however, the genes responsible for the different steps of apomixis i.e. apomeiosis, parthenogenesis and autonomous endosperm development have not yet been identified and may interact in a complicated manner. Therefore, although the potential of apomixis technology for plant breeding is widely recognised for already a long period of time, proof of concept is still awaited.

As yet another alternative, use can be made of reverse breeding technology as described in WO-03017753. Reverse breeding is based on the suppression of meiotic recombination through genetic engineering and the subsequent production of doubled haploid plants (DHs) derived from spores containing unrecombined parental chromosomes. These DHs differ with respect to their genetic composition solely as a consequence of the independent parental chromosome assortment which occurred during meiosis. Therefore, it is sufficient to make use of one co-dominant, polymorphic marker per chromosome to determine which of the DHs or lines derived therefrom should be combined through crossing to reconstruct the genetic composition of the original starting plant. As such, application of reverse breeding technology allows genetic preservation of any selected fertile plant through seeds even if its genetic composition is unknown.

However, a disadvantage of this technology is the fact that complete suppression of meiotic recombination results in the absence of chiasmata and thereby inappropriate chromosome segregation during meiosis I which could lead to aneuploidy of the gametes and thereby reduced viability. When no chiasmata are formed during meiosis I, every chromosome has an independent 50% chance to move to either one of the poles. This means that the theoretical chance to make a spore with a full chromosome complement is $(1/2)^x$ wherein x represents the haploid chromosome number. The frequency of balanced gametes therefore decreases with increasing haploid chromosome number.

Although many crop species have a relatively low chromosome number (e.g. cucumber has 7 chromosomes per haploid genome and spinach has only 6) there are also economically important species with relatively high chromosome numbers like tomato, one of the largest vegetable crops, which has 12 chromosomes per haploid genome. This technical constraint significantly reduces the efficiency of reverse breeding technology. Therefore, a clear need in the art exists for alternative methods which allow preservation of genetic composition in sexual offspring.

It is therefore the object of the present invention to provide a method for preserving the genetic composition of a parent organism, in particular a parent plant.

SUMMARY OF THE INVENTION

In the research that led to the present invention it was surprisingly found that by making use of plants regenerated from unreduced spores, for example as can be obtained as a result of a second division restitution (SDR) event, so-called "SDR-0 cells", it is possible to provide such method. This method can also be performed on other non-human organisms than plants, such as fungi or fish, and with other reproductive cells, such as gametes.

The invention thus relates to a method for producing a homozygous non-human organism from a heterozygous non-human organism, which homozygous organism can be crossed to obtain a hybrid, comprising:

a) providing a heterozygous starting organism;
b) allowing the organism to produce SDR-0 cells originating from second division restitution;
c) regenerating SDR-0 organisms from the SDR-0 cells; and
d) producing the homozygous organism from the SDR-0 organisms thus obtained.

This method will be called herein "Near Reverse Breeding".

Unreduced spores are formed preferentially as a consequence of the omission of the second meiotic division. This natural phenomenon is known as Second Division Restitution or SDR. SDR can occur during sexual reproduction in plants concomitantly with regular meiotic events. The Near Reverse Breeding technology of the invention exploits SDR events by specifically selecting unreduced spores that are produced through natural or engineered SDR for regeneration. The resulting plants, called SDR-0 plants, which are largely homozygous, are, in a preferred embodiment used to produce DHs. However, the level of homozygocity in the SDR-0 plants can also be increased through inbreeding steps or secondary SDR events or combinations thereof.

Molecular markers which are polymorphic between the paternal and maternal genomes of the starting plant can be used to identify those SDR-0 plants and DHs derived therefrom which are essentially complementary with respect to their genetic composition and which upon crossing result in the near complete reconstruction of the genetic make-up of the original starting plant.

The reconstruction is "near complete" as a consequence of meiotic recombination during the formation of the SDR-0 events and during the formation of the DHs derived therefrom. The reconstructed hybrids will genetically differ to some extent from each other as well as from the original starting hybrid plant. However, this variation is strongly reduced in comparison to a situation in which the DHs are derived directly from a regular meiotic event. Moreover, the DHs are genetically fixed which means there is no room for further selection.

The advantage of integrating an SDR event in this process is that the selection for genetic complementarity occurs in a two step process. The first step is concentrated on the proximal regions of the chromosomes i.e. including the centromeres. The second step is directed towards the distal ends of the chromosomes i.e those regions which were exchanged due to recombination. This delayed genetic fixation reduces the complexity and increases the chances of finding largely complementary genotypes especially when molecular markers are available for selection.

A further advantage of this approach is the fact that SDR is a natural process which occurs during sexual reproduction and which can be exploited as such without further need to interfere with sexual reproduction processes.

BRIEF DESCRIPTION OF THE DRAWINGS

The present invention will be further illustrated in the non-limiting examples that follow and that refer to the following figures:

FIGS. 3A, 3B-1, 3B-2, 3B-3, 3B-4 and 3B-5 show the formation of spores/gametes that occur in the plant that is regenerated from SDR-0 event 3 in FIG. 2.

FIG. 4 shows chromosome doubling in the spores which are formed.

FIG. 5 shows the AFLP Patterns of typical F2 plants of cucumber. Every horizontal line represents one individual plant. Every vertical column represents a linkage group. Light grey segments represent heterozygous areas, black and dark areas represent respective homozygous areas.

DETAILED DESCRIPTION

Figure 1A:
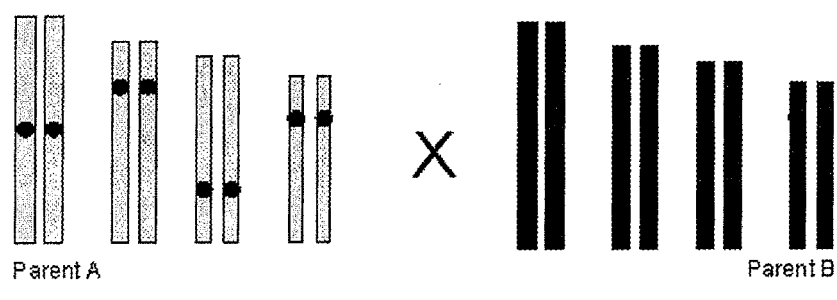
FIGS. 1A and 1B show the occurrence of a normal meiosis for 4 chromosome pairs of a completely heterozygous hybrid and the spontaneous doubling of the chromosomes after the reduction division took place (named "corresponding Doubled Haploids").
Figure 1A:
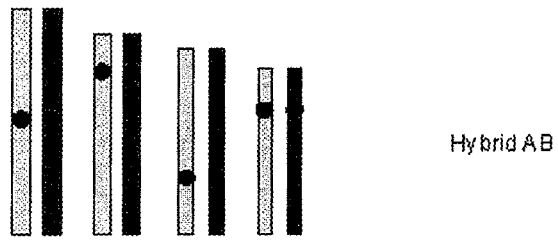
Figure 1A:
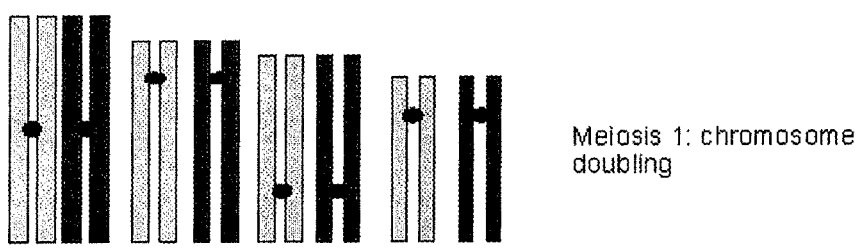
Figure 1A:
Figure 1B:
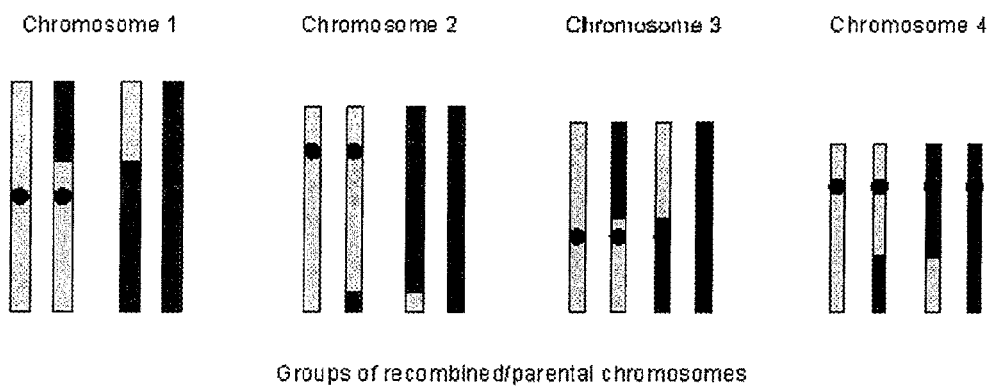
Figure 1B:
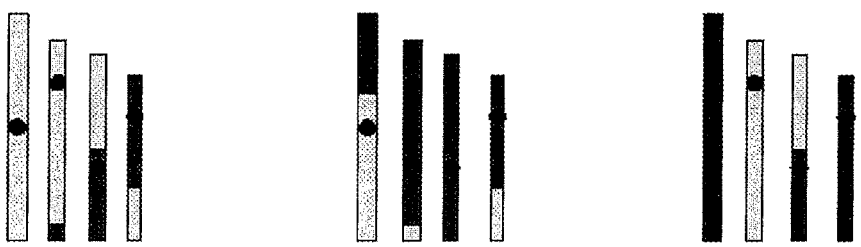
Figure 1B:
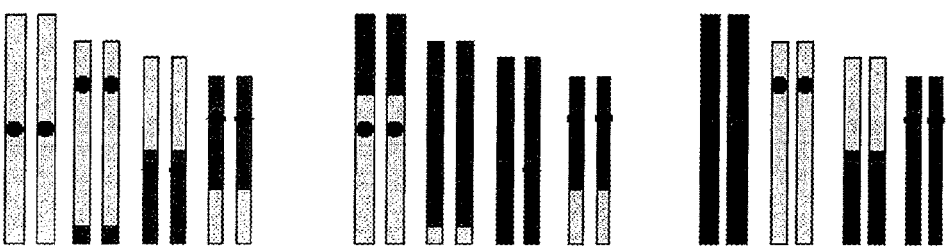
Figure 2:
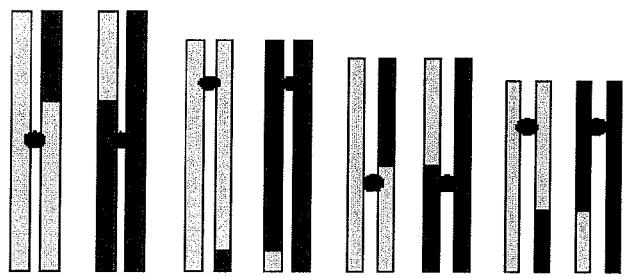
FIG. 2 shows a meiosis of the same heterozygous hybrid as in FIG. 1, but in the situation where the second division fails to take place (i.e. in case of Second Division Restitution).
Figure 2:
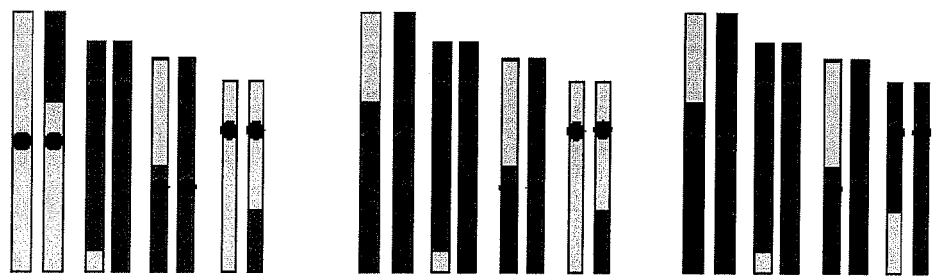
Figure 2:
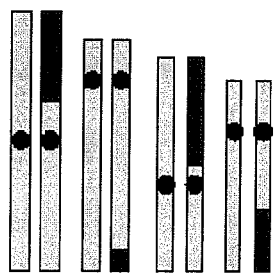
Figure 3A:
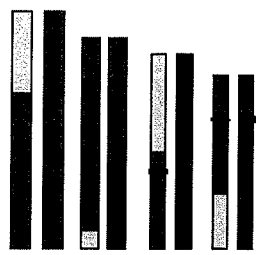
Figure 3A:
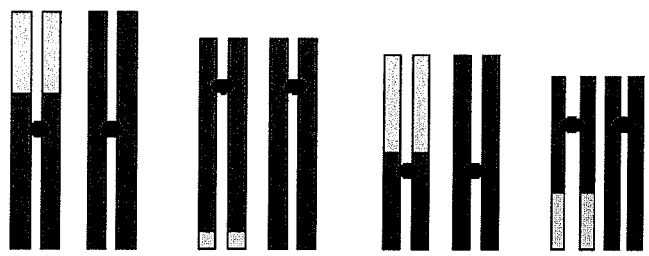
Figure 3A:
Figures 1, 3B:
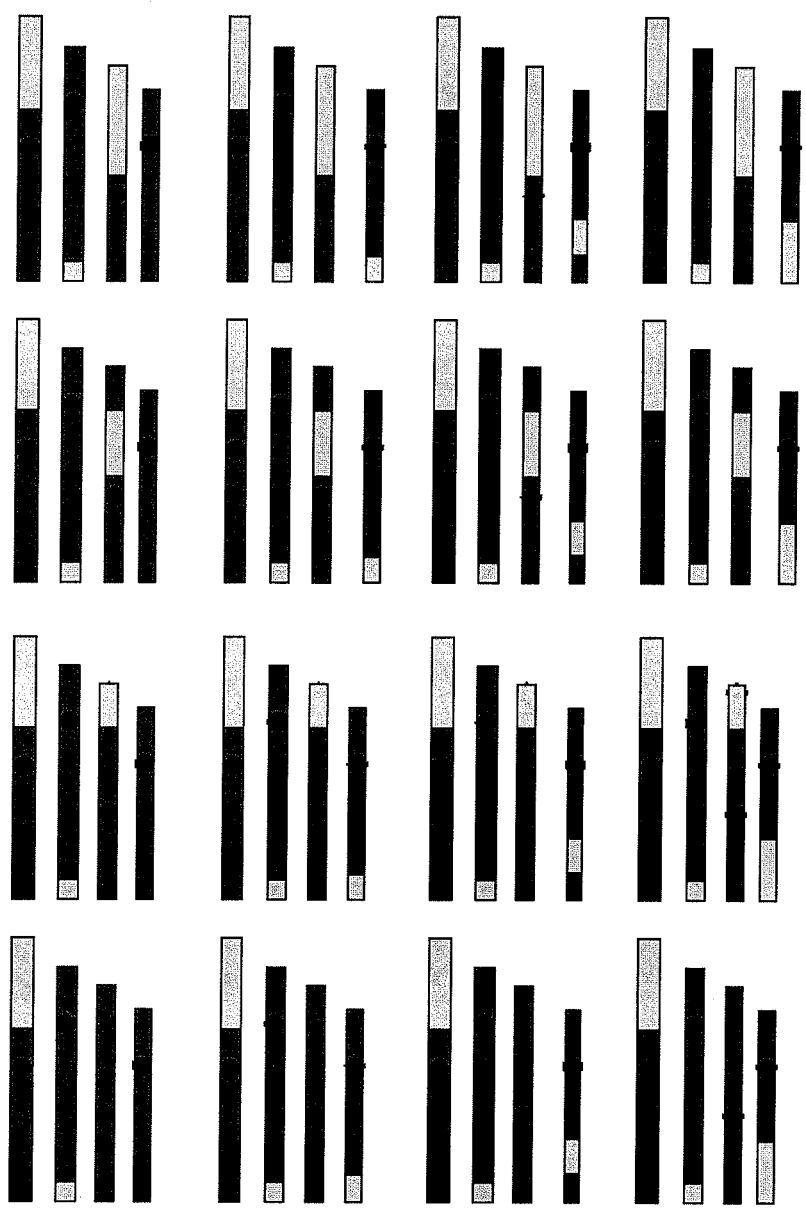
Figures 2, 3B:
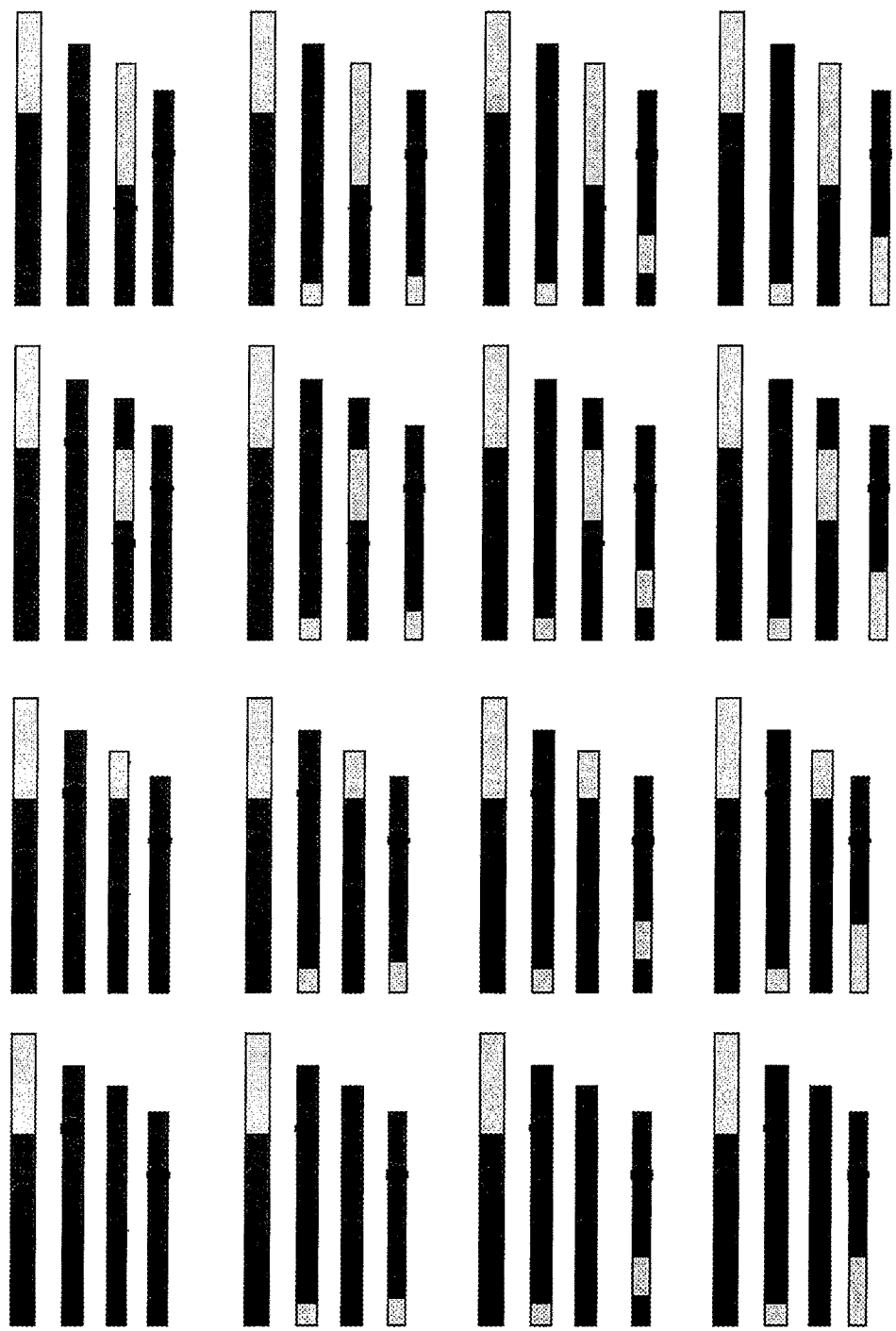

In greater detail, FIGS. 1 and 2 schematically illustrate the difference between a normal meiotic event (followed by the formation of DHs) and an SDR event. In both figures four chromosomal pairs have been depicted and the homologs are shown in light, respectively, dark rod like structures where the black circles on the rods depict the centromeres. The figures merely serve to illustrate the principle of this invention. It is obvious to those skilled in the art that in practice the number of chromosomal pairs involved depends on the species involved. Furthermore, the points of crossing-over are variable with respect to their number/chromosome and their position on the chromosome.

FIG. 1 depicts a normal meiosis and the doubling (which can be spontaneous or induced) of the chromosomes after both meiotic divisions took place. In this case crossing-over has led to the occurrence of two parental and two recombinant chromosomes per pair. In addition, due to the independent assortment of the two homologous chromosomes of each pair, it is obvious that many genetically different spores/gametes can be formed.

In FIG. 1, only three arbitrary outcomes of this process have been depicted. After regenerating plants from such spores, DHs can be obtained. The production of DHs is of utmost importance in contemporary plant breeding and is applied as an established technology for most crops. Plants regenerated from diploid spores will be further named DH-0 i.e. doubled haploid as the primary regenerant from a spontaneous or induced diploidized spore originating from a normal meiotic event. The term "SDR-0" is used for the primary regenerant from the cell or spore that lacked the second meiotic division. DH-0 plants when self-pollinated will give rise to progeny (DH-1) plants which are genetically 100% identical and completely fixed in all the alleles. So, although the spores (gametes) that are formed on the DH-0 plants underwent again meiosis and recombination, no genetic rearrangements can take place. This therefore means that this so-called "pure line" is immortalised by the fact that no segregation can take place. Such a line can however phenotypically show different appearance when grown in different conditions such as low or high temperatures, or for instance in different climatic zones. The differences that can be observed are however valid for all "members" of the line in other words there will be no "intra-line" variation. There may, however, be differences between different pure lines (DH-1), which is called "inter-line" variation.

FIG. 2 depicts an SDR event. In contrast to FIG. 1 where a spontaneous or induced chromosome doubling took place after completion of meiosis, the occurrence of diploid spores is caused by the absence of the second meiotic division.

The fundamental difference between DHs and diploid SDR plants is illustrated by the fact that heterozygous segments are present on the different chromosomes in the SDR plant, whereas DHs are fully homozygous. It should further be noted that in SDR plants all chromosomal pairs are homozygous with respect to their centromeric regions. Heterozygocity if present, resides at the distal chromosomal ends. This contrasts to another aberrant meiotic event called First Division Restitution or FDR which is characterised by the absence of the first meiotic division and which results in heterozygocity at the centromeric regions for all chromosomal pairs.

In the theoretical case shown in FIG. 2, the starting plant (donor-plant) that was used to generate DHs and SDRs, respectively, contains homologous chromosomes that are completely heterozygous. This means that all alleles of the genes carried by those chromosomes are polymorphic. In practice however this is highly unlikely and therefore this case exemplifies the most extreme heterozygous situation.

From FIG. 2 it is also clear that for an SDR event the crossing-over points of each chromosomal pair determines the ratio between homozygous loci and heterozygous loci. This ratio increases for those SDR-events which on average have their crossing-over positions located more towards the telomere whereas it decreases when on average the crossing over positions are located more towards the centromer. With the availability of sufficient molecular markers these crossing-over points can easily be determined for each SDR event.

The extent of crossing-over for each chromosomal arm is limited by the position of the centromere. It should further be noted that in case the residual heterozygocity is relatively low the SDR events resemble the occurrence of RIL's and BIL's but in heterozygous forms.

SDR is just one form of a broader class of phenomena leading to the formation of unreduced spores/gametes (Veilleux, Plant Breeding Reviews 3, 253-288 (1985)) describes the mechanisms by which unreduced gametes are formed and provides a list of the occurrence of unreduced gametes in crops plants. At that time mainly two different classes of unreduced gametes were recognised namely SDR and FDR. Recently a third class of unreduced gametes has been published named Indeterminate Meiotic Restitution or IMR (Lim et al. (2001) Theor. Appl. Genet. 103: 219-230).

For the purpose of this invention only SDR is relevant. SDR occurs naturally in a wide variety of crops as is evidenced by the list presented by Veilleux, supra, and other independent research (Lim K et al. (2004) Breeding Science 54: 13-18). Interestingly, it was found that in pepper the frequency of SDR 2 n gametes (pollen) increased from less than 1% to up to 10.5% (average) by 48 hours exposure of the plants to 11° C. (Zhang X et al. (2002) Journal of Horticultural Science & Biotechnology 78: (1) 84-88). The maximum frequency of SDR occurrence was measured to be 81.3%. It is thus possible to increase the number of SDR events by external stimuli.

The occurrence of 2 n spores or gametes is not restricted to the male gametophyte but there is also evidence that it occurs at the level of the female gametophyte. For example Zagorcheva L (Genetics and Plant Breeding 9(5), 386-399 (1976)) reported the occurrence of deviations of macrosporo- and macrogametogenesis in cucumber.

Near Reverse Breeding exploits the occurrence of unreduced spores which are the result of SDR in order to reconstruct the genetic composition of heterozygous starting plant material to a large extent. Basically, in order to reconstruct the original hybrid plant one starts to select those SDR-0 plants which are complementary for the centromeric region of each chromosome. This can be achieved by genotyping the centromeric region for each chromosome using polymorphic molecular markers. As SDR-0 regenerates are homozygous at the centromeric region for each chromosome, fully (or partly) complementary plants can readily be identified in this way. The probability to find a complementary SDR-0 plant (on the basis of centromere complementarity, and without taking any residual heterozygocity into account) when 1 random SDR-0 plant has been selected is $(½)^x$ where x is the number of chromosomes.

In case the original parental lines are to be reconstructed, the probability of finding one parent is $(½)^{x-1}$ and for the other parent the probability is $(½)^x$. As stated earlier, such "near parental" lines can also be considered to be Back-cross Inbred Lines (BIL's) whereby the introgression segments are generated for both parents. These complementary plants can subsequently be crossed in order to reconstruct the genotype of the original hybrid plant.

However, since, due to meiotic recombination, the distal regions of the chromosomal arms of the SDR-0 plants will be heterozygous (in case of a single crossing-over per chromosome arm) segregation will occur in the reconstructed hybrid which may lead to a certain level of non-uniformity. When the genetic information located in the distal regions of the complementary SDR-0 events is not contributing significantly towards phenotypic variation because recombination has occurred at relatively distant chromosomal positions and therefore gene content is low or because the allelic variation does not contribute significantly to phenotypic variation, the reconstructed hybrid will be relatively uniform.

In a preferred embodiment of the invention SDR-0 events are generated in which the meiotic recombination occurred exclusively at the extreme telomeric regions of the chromosomes. In such events the chromosomes have been physically recombined but not genetically.

Figures 3, 3B:
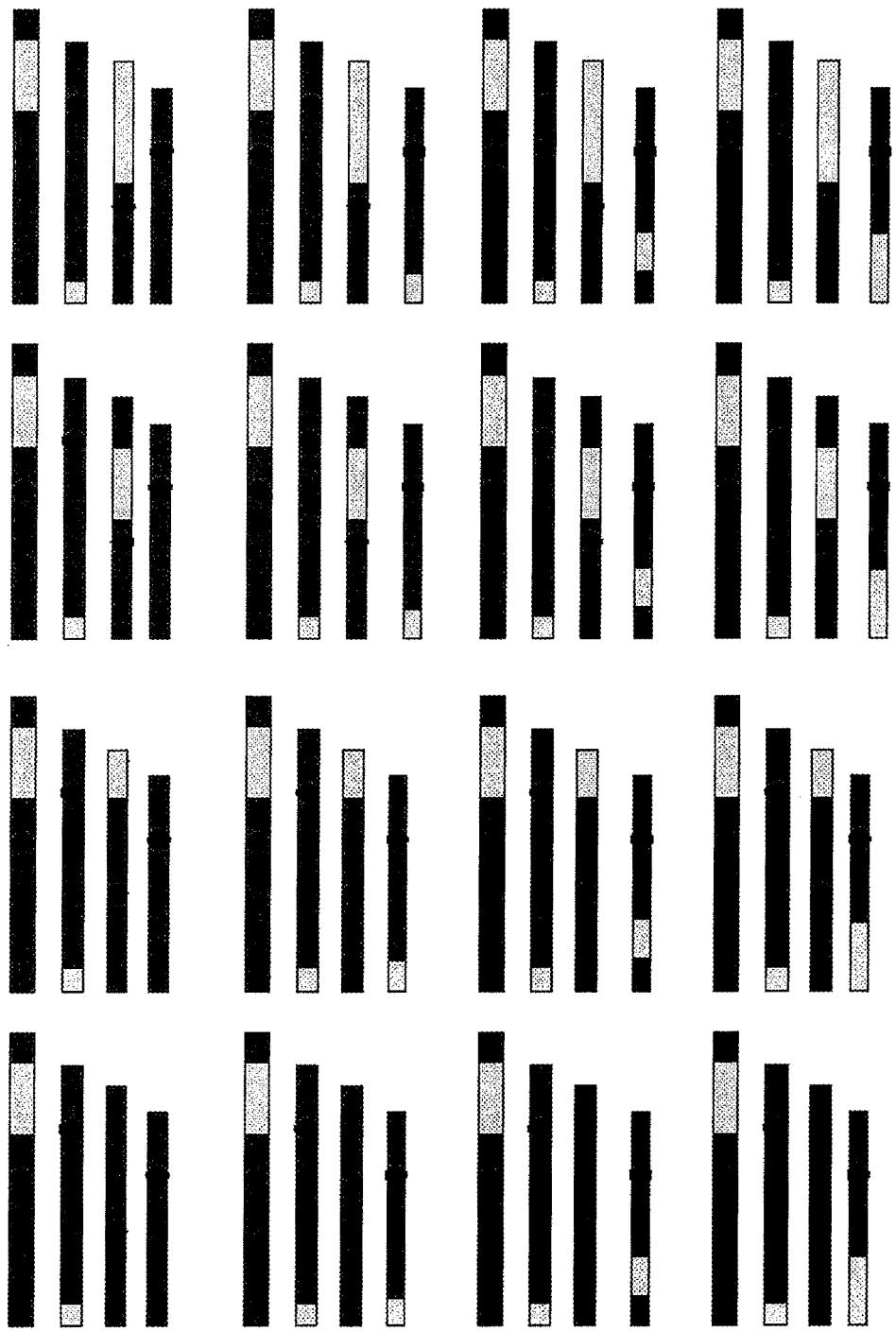

In order to obtain genetically fully homogeneous reconstructed hybrid plants, DHs are produced from each of the complementary SDR-0 events. This principle which is schematically illustrated in FIG. 3 depicts the formation of spores/gametes that would occur for the plant that is regenerated from SDR-0 event 3 from FIG. 2.

Figures 3, 3B, 4:
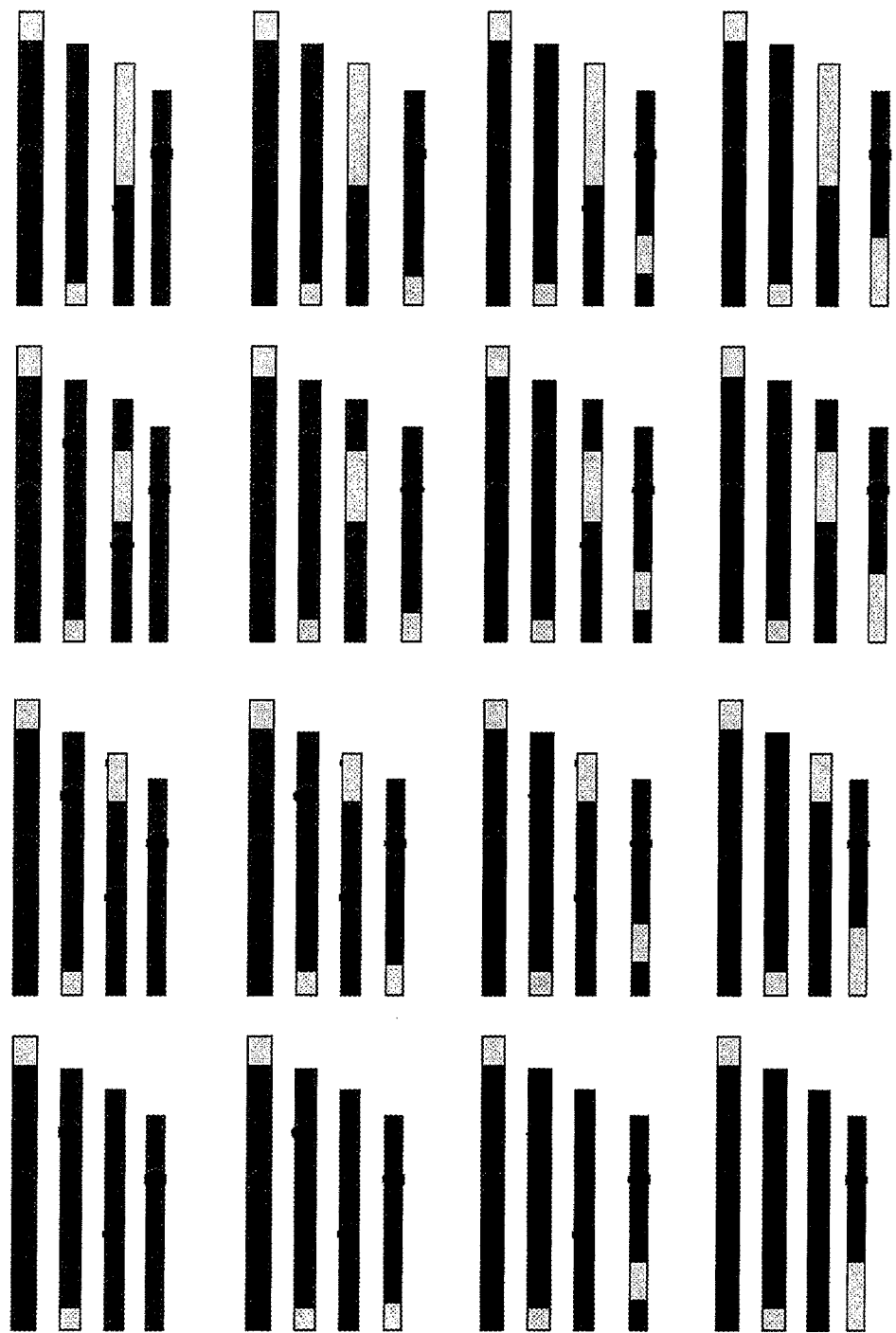

The spores which are formed can be regenerated and upon chromosome doubling DHs can be produced. By using molecular markers one can select those DHs which are genetically very similar to either one of the parental lines. This is illustrated in FIG. 4 by the chromosomal set which has been doubled.

Due to segregation, the distal ends of the chromosomes (from the recombination break point to the telomer) of these doubled haploid plants will on average contain 50% of the genetic information of each parent. When two randomly chosen doubled haploid plants derived from complementary SDR-0 events are combined through crossing, the proximal arm regions will be 100% heterozygous whereas the distal arm regions will be 50% heterozygous in the reconstructed hybrid plant. As SDR-0 events are assumed to be 60% homozygous on average (Carputo, D. et al. (2003) Genetics 163, 287-294), reconstruction with complementary events will result in 80% heterozygocity on average (100%×60%+ 50%×40%) and 20% homozygocity. The homozygocity between the proximal and distal crossing-over point will be skewed to the genotype of the SDR-0 regenerant which was homozygous for this region, whereas distal to the distal crossing-over point, the homozygocity will be equal for both parental genotypes.

It is clear to the person skilled in the art that the mentioned figures relating to the percentages of heterozygocity represent extreme values i.e. starting from a plants which is 100% heterozygous which means all alleles of the genes carried on the chromosomes are polymorphic. In practice this is highly unlikely and therefore the percentages of heterozygocity will on average be lower.

The invention further relates to a method for producing a hybrid, comprising crossing a first homozygous organism that is produced according to the invention with a second homozygous organism. According to the invention it is possible to reconstruct the genetic make-up of the original hybrid whereas, in addition, variants can be obtained which approach the genetic make-up of the original hybrid.

In a first embodiment, the second homozygous organism is at least partially complementary to the first homozygous organism such that the resulting hybrid resembles the heterozygous starting organism. Suitably, the resemblance with the heterozygous starting organism comprises the hybrid having at least 50% of the heterozygosity of the starting organism. Preferably, the resemblance in heterozygosity is any percentage between 50 and 100%, more specifically the resemblance in heterozygosity is any percentage between 50% and 60%, preferably between 60% and 70%, more preferably between 70% and 80%, even more preferably between 80% and 90% and most preferably between 90% and 100%. The phrase "any percentage" is intended to cover each and every percentage within the stated range even though the particular percentage is not explicitly mentioned.

Alternatively, the second homozygous organism is selected such that the resulting hybrid outperforms the original heterozygous starting organism. The "original heterozygous starting organism" is the organism that is used in step a) of claim 1. "Outperforms" means that the hybrid has improved characteristics over the starting organism. For example, in the case of a plant, the hybrid may have larger fruit, more fragrant flowers, and the like.

The variation of the relative level of homozygocity as well as its parental origin in the reconstructed hybrid plant depends on the crossing-over point within each chromosomal arm of each parent. By using molecular markers both SDR-0 events as well as DHs derived therefrom can be selected which upon hybridisation result in F1 hybrids with relatively low levels of homozygocity.

In this embodiment, for the SDR-0 events one should select for those having on average more distal crossing-overs whereas for the DHs one should select those being most complementary.

On the other hand, however, it may be desirable to select those events which have a relatively large distance between the proximal and distal crossing-over point to introduce homozygocity in the F1 hybrid which can be skewed to either parent.

From the above it is clear that Near Reverse Breeding enables a plant breeder to reconstruct a hybrid plant to a large extent but that significant variation due to different levels and origins of the alleles which are homozygous can also be obtained between the experimental F1 hybrids which may result in improvement of the performance of the original (starting) hybrid plant.

In addition, it is possible to produce hybrids which are complementary only for a given subset of chromosomes. This can be done by selecting those SDR-0 events which on the basis of their centromeric genotype are complementary for the desired chromosomal pairs and identical for the others. Such hybrids produced from so-called near-substitution lines will be largely homozygous for non-complementary chromosomal pairs with similar levels of heterozygocity at the distal regions of the chromosomes as compared to the complementary chromosomal pairs. In its most extreme form, fully non-complementary double haploids can be crossed which leads to hybrid plants with heterozygocity limited to the distal parts of the chromosomes.

In order to exploit SDR for Near Reverse Breeding technology, use can be made of the spontaneous occurrence of SDR events or one can induce SDR events through e.g. genetic engineering.

Another embodiment of the inventions relates to backcrossing. Backcrossing is a plant breeding term which is well known to the person skilled in the art and which refers to a procedure in which a specific trait is introgressed into a plant line with a desired genetic make-up (the so-called genetic background). The desired outcome of this procedure is a plant line which is genetically nearly identical to the starting plant line but to which only the genetic factors underlying the desired trait are added through recombination. In order to achieve this objective the plants carrying the desired genetic background and the desired trait are crossed and the offspring is selected for plants carrying the trait as well as, as much as possible of the genetic background. As with each backcross cycle the increment of the desired genetic background is on average halved, in practice it takes 4 to 5 breeding cycles to complete the backcrossing procedure.

Near reverse breeding allows to speed up backcrossing as the procedure to reach homozygocity takes only two steps. The first step is identical to a traditional backcrossing procedure i.e. crossing of the plants carrying the desired genetic background and the desired trait. The resulting hybrid is used to generate SDR-0 events which are selected for the desired trait which can be based on the phenotype or marker assisted and the desired genetic background based on centromer markers specific for the genetic background.

The second step involves the production of DHs which are selected for the maximum amount of genetic background using molecular markers. Near reverse breeding fastens the procedure to come to homozygocity but allows two selection steps. When sufficient genetic markers are available the desired backcrossing product can be obtained much more efficient as compared with the traditional procedure as the number of time consuming breeding cycles can significantly be reduced.

With the near reverse breeding method of the invention CMS can be introgressed into a desired background in a very efficient manner. In order to apply near reverse breeding for CMS transfer, the CMS donor line is preferably genetically dissimilar to the line that has to be converted to male sterility for a large number of nuclear genetic markers so that the difference between the chromosomes of the CMS and the fertile donor can be more easily determined.

In order to convert a pure line or a desired inbred line (homozygous or nearly homozygous) into a similar line but with a CMS background, a first cross is made by pollination of the said CMS with pollen of the desired line. The resulting F1 progeny contains CMS and 50% of the chromosomes of the desired line. The F1 progeny plants are induced to perform SDR-meiosis during gynogenesis either by treatment with chemicals such as nitrous oxide or stress conditions such as low temperature. SDR may also occur spontaneously during gynogenesis.

In case androgenesis is applied, use has to be made of a restorer gene which can suppress the effect of the male sterility inducing cytoplasm.

The resulting SDR-0 plants are genetically analysed using DNA markers which are polymorphic for the centromeric regions of the F1 hybrid. SDR-0 plants which exclusively contain the centromeric regions of the line which has to be converted into a CMS are selected. In case large numbers of discriminating markers covering the genome are available, one can select for those SDR-0 events which on average have the most proximal crossing over positions on the chromosomes. This largely converts a selected line into a CMS in a single step. If needed, this backcross cycle can be reiterated.

The spontaneous occurrence of SDR events may be enhanced by specific abiotic stress conditions such as heat or cold shocks. Such stress conditions are known to enhance the formation of unreduced, diploid spores (Zhang X et al., (2002) Journal of Horticultural Science & Biotechnology 78: (1) 84-88). In addition, it is possible to induce the formation of 2 n pollen by applying nitrous oxide ($N_2O$) gas (Okazaki, K. et al. (2005) Euphytica, 143, 101-114).

When diploid spores are produced through male meiosis it is also possible to enrich for these cells through flow cytometry and fluorescence activated cell sorting. Such technologies are in itself well known to the person skilled in the art and have been applied to microspores in the past (Deslauriers C et al., (1991) Flow cytometric characterisation and sorting of cultured *Brassica napus* microspores. Biochem. Biophys. Acta: 1091, 165-172).

In addition, it is known that diploid spores or pollen are larger in size than their haploid peers (Lernmi G and Negri V. (1994) Research on 2 n pollen production in *Lotus* tenuis an I.M.G.V. of Perugia University. *Lotus* newsletter Vol; 25, pp 24-27). Surprisingly, the mere fact that diploid spores are physically different from haploid spores makes it possible to enrich specifically for diploid spores through flow cytometry and fluorescence activated cell sorting.

Furthermore, the optimisation of the environmental conditions which lead to the formation of diploid spores can easily be done using the different sorting technologies.

Regeneration of the unreduced spores may occur through androgenesis, gynogenesis or parthenogenesis by prickle pollination in a manner similar to the regeneration of reduced spores. In case parthenogenesis by prickle pollination is applied, it may be advantageous to use diploid pollen, especially for those species which have a low tolerance for modifications of the ratio of maternal to paternal genomes in endosperm. For most, if not all crops these regeneration protocols are described in the literature and known to the person skilled in the art.

Once plants are regenerated from diploid spores, molecular markers can be used to determine whether or not the centromeric regions of the chromosomal pairs are homozygous or heterozygous which is diagnostic for SDR or FDR events, respectively. In this way SDR events can be readily selected.

Different genetic approaches are known to a person skilled in the art which allow interference with gene functions involved in the second cell division of meiosis. Such interference can either be through mutagenesis or transgenesis. Transgenic approaches aim at the stable or transient introduction of a DNA fragment which modifies the second division of meiosis leading to diploid spores of the SDR type. This modification can occur through interference with genetic factors involved in meiotic processes especially those involved in the second cell division. The interference can be established through specific down-regulation of gene expression based on post-transcriptional gene silencing (PTGS). PTGS can be achieved through RNA-interference (RNAi) or virus-induced gene silencing (VIGS).

Yet in another approach, the interference can be established through the over-expression of proteins which exert a dominant negative effect on the second division of meiosis leading to SDR.

Irrespective of the approach taken, the target gene needs to be known at the molecular level. A number of recessive mutants have been described of potato (pcpc, osos, fcfc) which result in an SDR-type of meiosis (Carputo, D. et al (2003) Genetics 163, 287-294). Also for maize the elongatel mutation leads to the absence of meiosis II (Barell, P J and Grossniklaus, U. (2005) Plant J. 43, 309-320).

Although the genes which have been mutated in these specific examples have not yet been identified at the molecular level the skilled person will be able to do so and therefore these and other yet unknown genes are excellent candidates to achieve SDR in target species using molecular suppression technologies. The present invention relates to the general principle of near reverse breeding and the fact that not all possible embodiments of inducing SDR in a starting organism have been described is not relevant for the invention.

Alternatives to the genes described above can be found in genes like DUET (Venkata Reddy et al. (2003) Development 130, 5975-5987) and CYC1;2 (Wang et al. (2004) Plant Physiology 136, 4127-4135) which have been described for *Arabidopsis thaliana* and which upon mutation lead to an aberrant form of meiosis.

The diploid meiotic products in these mutants are SDR-like and therefore DUET and CYC1;2 as well as their functional homologues in other plant species are candidate target genes to achieve an SDR-type of meiosis.

Yet another candidate target gene is TETRASPORE/STUD (Yang et al (2003) Plant J. 34, 229-240) which upon knock out leads to absence of cell division after meiosis. Diploid regenerants of microspores of a tetraspore/stud mutant can be SDR-like.

Once SDR-0 plants have been obtained they can be further characterised molecularly. Initially, the haplotypes of the centromeric regions can be determined which provides insight in the level of complementarity of the homologous chromosomes between the SDR-0 plants. Depending on the application one can select fully or partially complementary SDR-0 plants. The SDR-0 plants may subsequently be used to generate denser haplotype maps. This can be achieved using molecular typing technologies well known to the person skilled in the art. Examples are RFLP (Restriction Fragment Length Polymorphism (Beckmann, J. S, and Soller, M (1983) Theor. and Appl. Genet. 67, 35-43)), RAPD (Random Amplified Polymorphic DNA (Welsh, J. and McClelland, M. (1990) Nucleic Acids Res. 19, 961-866)), AFLP (Amplified Fragment Length Polymorphism (Vos, P. et al (1995) Nucleic Acids Res. 23, 4407-4414)) or SFP (Single Feature Polymorphism (Borovitz, J. et al (2003) Genome Research 13, 513-523). These technologies can be used without prior knowledge of the nature of the DNA polymorphisms.

In case the DNA polymorphisms are characterised e.g. as SNPs use can be made of a plethora of SNP detection technologies (Kwok, P. Y. and Chen, X (2003) Curr. Issues Mol. Biol. 5, 43-60). The haplotype maps can be used to select plants for DH production. The DHs obtained can be haplotyped for the regions which were heterozygous in the SDR-0 starting plant. Such analysis provides the genetic information which can be used to steer the ratio heterozygocity/homozygocity in the F1 hybrid and it provides the possibility to select for either of the parental origins of the homozygous regions of the genome of the F1 hybrid.

The probability of finding at least one complementary combination of two homozygous organisms (a combination that after crossing can 'resynthesize' the starting organism), is a function of the haploid chromosomal number x of a given species and the number k of homozygous organisms produced from a heterozygous starting organism in which SDR has taken place.

When the haploid chromosomal number of a given crop species is expressed as x, the maximum number of SDR-0 genotypes, considering only the chromosomal regions proximal of the crossing over points and thus including the centromeric region, which are obtained from a plant of that crop species is $2^x$. The probability that one randomly chosen pair of SDR-0 plants, or a DH plant derived therefrom, from this population will, upon crossing, result in an F1 hybrid which has a genotype near identical to the genotype which produced the SDR-0 events (original genotype) is $(2^x-1)/2^x$. In case a total number of k SDR-0 plants is produced, there exists a number of $\frac{1}{2}k(k-1)$ combinations of 2 genetically distinct SDR-0 plants or DH plants derived therefrom which can be crossed. The probability for any randomly chosen combination of 2 SDR-0 plants or DH plants derived therefrom to be complementary is $\frac{1}{2}^x$. Thus, the probability for any randomly chosen combination of 2 SDR-0 plants or DHs therefrom that they are not complementary is $1-\frac{1}{2}^x=(2^x-1)/2^x$. In case of k SDR-0s or DHs derived therefrom, $\frac{1}{2}k(k-1)$ combinations can be made and therefore the probability that within this SDR-0-population or DHs derived therefrom no complementary plants can be found is $((2^x-1)/2^x)^{(1/2k(k-1))}$ and therefore the probability that at least one complementary combination of two SDR-0 plants or DHs derived therefrom can be found is $1-((2^x-1)/2^x)^{(1/2k(k-1))}$. The result of this analysis is shown in table 1 below.

TABLE 1

Probability of finding at least one combination of two complementary SDR-0 or DHs derived therefrom, using near reverse breeding technology as a function of the haploid chromosome number x and the number of available randomly produced SDR-0 plants k

| | k | | | | | | | | | |
|---|---|---|---|---|---|---|---|---|---|---|
| x | 2 | 4 | 8 | 16 | 24 | 32 | 48 | 64 | 128 | 256 |
| 7 | 0.008 | 0.046 | 0.197 | 0.610 | 0.885 | 0.980 | 1.000 | 1.000 | 1.000 | 1.000 |
| 9 | 0.002 | 0.012 | 0.053 | 0.209 | 0.417 | 0.621 | 0.890 | 0.981 | 1.000 | 1.000 |
| 11 | 0.000 | 0.003 | 0.014 | 0.057 | 0.126 | 0.215 | 0.424 | 0.626 | 0.981 | 1.000 |
| 12 | 0.000 | 0.001 | 0.007 | 0.029 | 0.065 | 0.114 | 0.241 | 0.388 | 0.863 | 1.000 |

This analysis shows that the original genotype can be largely resynthesized as an F1 hybrid according to the present invention with high probability using 48 SDR-0 plants or DHs derived therefrom for plant species with a haploid chromosomal number of 7 like cucumber, 128 for a plant species with a haploid chromosomal number of 9 like cauliflower and 256 for a plant species with a haploid chromosomal number of 12 like tomato, melon and sweet pepper. These figures illustrate the fact that the number of SDR-0 plants required for applying near reverse breeding for these crop species is relatively low and therefore the generation of such numbers is highly feasible, especially in an industrial environment. It is obvious to the person skilled in the art that such calculations can be made for any plant species for which the haploid chromosomal number is known.

"SDR-0 plants or cells" as used in this application is intended to relate to the plants and cells resulting from unreduced gametes. Such unreduced gametes may in turn be the result of a Second Division Restitution (SDR) event, but may also be the product of an aberrant form of meiosis which leads to diploids.

The invention thus provides the means to use organisms, in particular plants, and their progenies, regenerated from SDR or SDR-like unreduced gametes, for example for the purpose of genotype reconstruction, for producing near complementary parental lines, for making near chromosome substitution lines and for optimizing F1 hybrids by introduction of homo- and heterozygous genomic segments.

Figures 3, 3B, 4, 5:
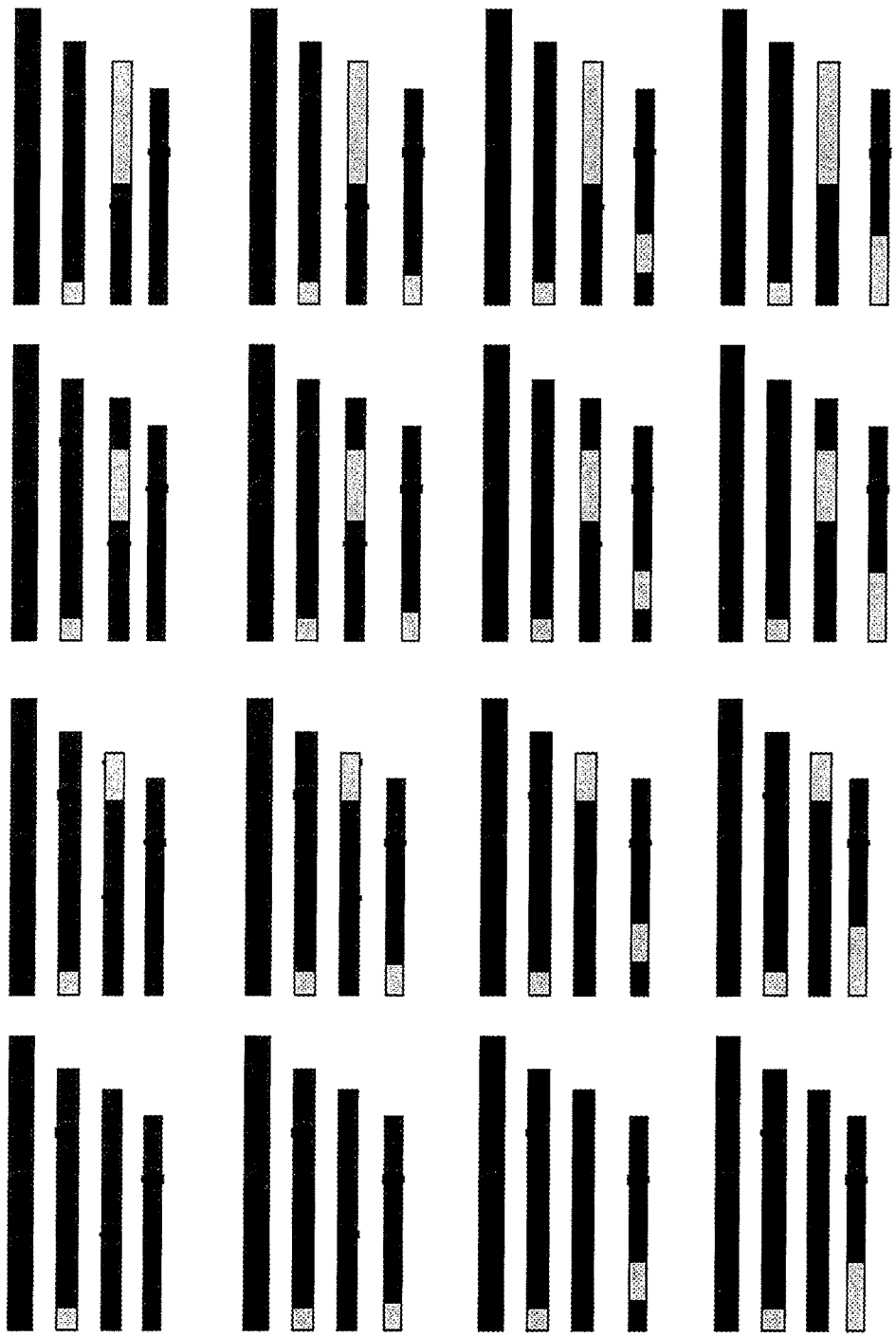
Figure 4:
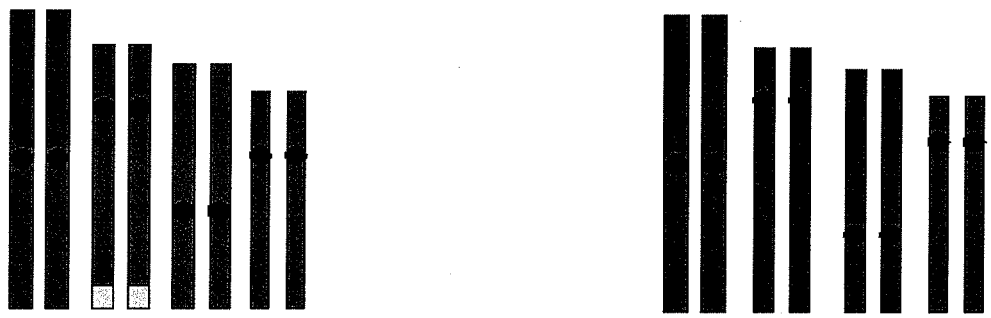
Figure 5:
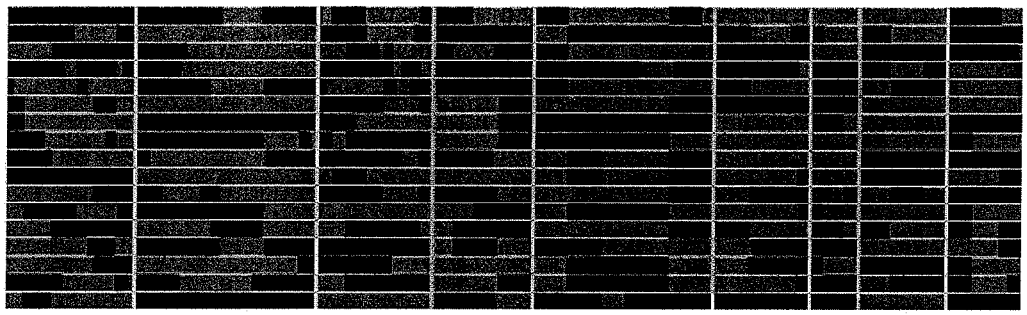

FIG. 5 shows the AFLP Patterns of typical F2 plants of cucumber. Every horizontal line represents one individual plant. Every vertical column represents a linkage group. Light grey segments represent heterozygous areas, black and dark areas represent respective homozygous areas.

Figure 6:
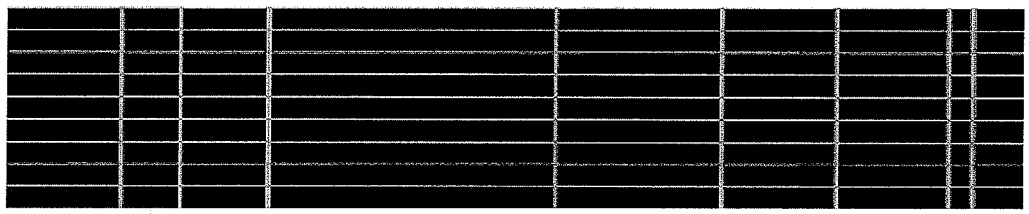
FIG. 6 shows the AFLP analysis of typical DH lines of cucumber. Every horizontal line represents one individual plant. Every vertical column represents a linkage group. Only black and dark areas are present as expected in DHs Light grey segments are absent.

FIG. 6 shows the AFLP analysis of typical DH lines of cucumber. Every horizontal line represents one individual plant. Every vertical column represents a linkage group. Only black and dark areas are present as expected in DHs Light grey segments are absent.

Figure 7:
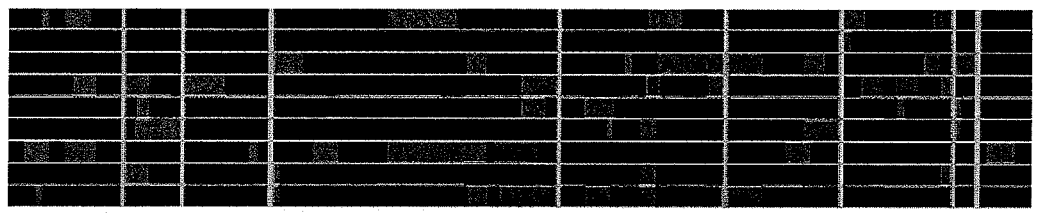
FIG. 7 shows the AFLP analysis of typical SDR-0 plants in cucumber. Every horizontal line represents 1 individual plant. Every vertical column represents a linkage group. Light grey segments represent heterozygous areas, black and dark areas represent respective homozygous areas.

FIG. 7 shows the AFLP analysis of typical SDR-0 plants in cucumber. Every horizontal line represents 1 individual plant. Every vertical column represents a linkage group. Light grey segments represent heterozygous areas, black and dark areas represent respective homozygous areas.

Figure 8A:
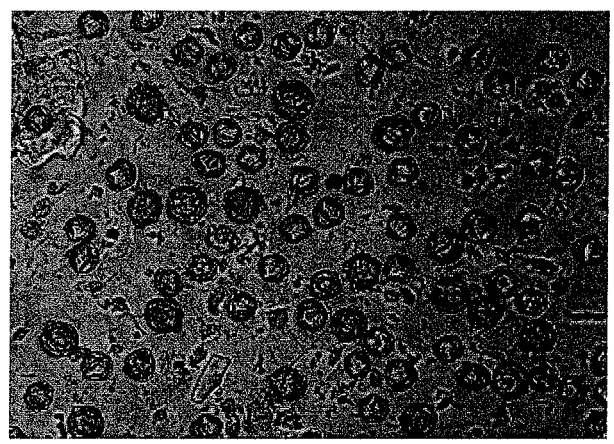
FIGS. 8A and 8B show representative examples of the morphologies of pollen collected from cold-treated plants (FIG. 8A) versus control plants (FIG. 8B).
Figure 8B:
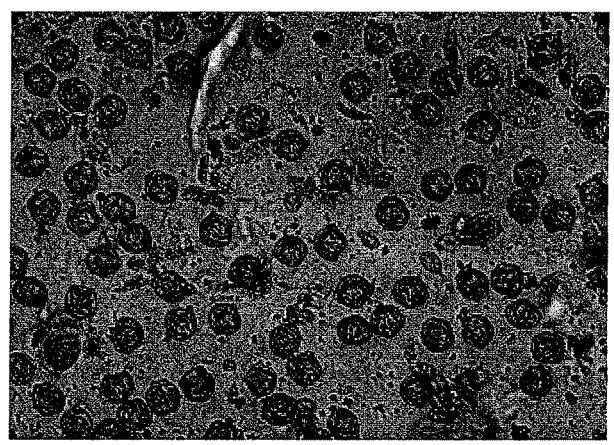

FIG. 8 shows pollen collected from pepper plants treated with low temperature. Panel A represents the pollen of the cold-treated plants whereas panel B represents the pollen of the control plant as observed through the light microscope.

EXAMPLES

Example 1

Demonstration of the Occurrence of a Relatively Low Level of Heterozygocity in Cucumber (*Cucumis Sativus* L.) Plants Obtained Through Gynogenesis By making haploids and doubled haploids in cucumber according to EP-374755 it was found by using AFLP analysis (carried out according to EP-534858) that among the expected doubled haploids, a certain percentage proved to be not originated from haploid megaspores but rather to be derived from an unreduced megaspore (2 n). This is well demonstrated in FIGS. 5, 6 and 7 which shown that the originally presumed doubled haploids (FIG. 6) still contain heterozygous sectors, which by definition is not possible in true doubled haploids.

This example shows that through gynogenesis in cucumber DHs can be obtained but that in addition plants are obtained which show some regions which are heterozygous. This level of heterozygocity is strongly reduced as compared to the F2 generation and is therefore most likely caused by an SDR-like mechanism.

Example 2

Enhancement of the Formation of Unreduced Spores/Gametes in Sweet Pepper (*Capsicum Annuum* L.)

In order to increase the frequency of unreduced spore/gamete formation, cold stress was applied as an inducer. For this purpose, flowering plants of sweet pepper containing pre-meiotic floral buds and growing at 23° C. were exposed for 5 days to 11° C. according to Zhang et al. (2002) *Journal of Horticultural Science & Biotechnology* 78, 84-88. After this cold shock, the buds were harvested and pollen was extracted by opening the anthers using dissecting forceps and scalpel. The pollen were subsequently transferred on a microscopic glass slide and stained for viability using a drop of aceto-carmine. Cover slides were put on top of the suspension which was investigated using light-microscopy. As a control, pollen was collected form sweet pepper plants which were grown at 23° C.

FIG. 8 shows representative examples of the morphologies of the pollen collected from the cold-treated plants (8A) versus the control plants (8B). As can be seen, the number of pollen with an increased size indicative for being derived from unreduced spores is strongly increased for the cold-treated plant. In this particular example it was estimated that the % of unreduced spores mounted up to 25 due to the cold treatment. As such the enhancement of the formation of unreduced spores by temperature stress is shown to be highly feasible.

Example 3

Enrichment of Naturally Occurring Diploid Spores in Broccoli (*Brassica Oleracea* L.) Through Flow Cytometry For broccoli (and other plant species) it is known that diploid spores are larger than haploid spores. In order to determine whether it is feasible to enrich for diploid spores using flow cytometry different mixtures were made of spores obtained from diploid and tetraploid plants. Spores were isolated by grinding floral buds (3-4 mm in size) in a buffer solution (8.2 g/L NaCl, 1.9 g/L $Na_2HPO_4.2H_2O$, 0.3 g/L $NaH_2PO_4.2H_2O$, pH=7.4) and subsequent filtering through a 110 µM filter. The cells were washed twice with the extraction buffer and counted.

Figure 9:
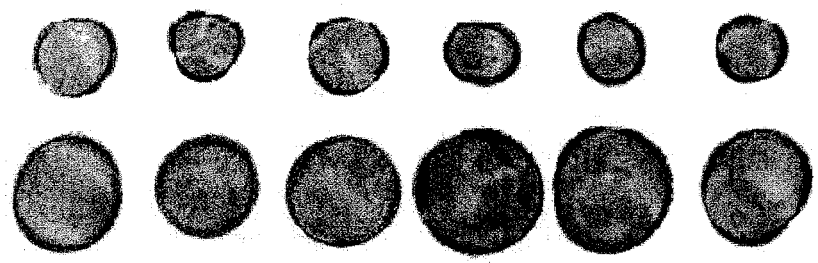
FIG. 9 shows the purified diploid microspores (lower row) obtained in this experiment compared to normal haploid microspores as observed through a light microscope.

The following mixtures were made of haploid versus diploid cells: 1:1, 10:1 and 100:1. Sorting was carried out on the basis of the parameters granularity, vitality and size. Enrichment of diploid cells was obtained for all ratios and based on each of the three parameters. In a next experiment a natural population of haploid microspores was sorted based on the above mentioned parameters. It was found that diploid microspores could be sorted which were estimated to be present in a frequency of 0.7% in the microspore population. FIG. 9 shows the purified diploid microspores (lower row) obtained in this experiment compared to normal haploid microspores as observed through the light microscope. Pictures were obtained by courtesy of Ing. M. Vennik; TNO Leiden (The Netherlands).

Example 4

Construction of RNA Interference Vectors which can be Used to Downregulate Candidate Target Gene Tetraspore In order to downregulate the activity of a candidate target gene in a particular plant species, use can be made of RNA interference. For that purpose DNA fragments of the Tetraspore of *Arabidopsis thaliana* were inserted into pKANNIBAL (Wesley et al. (2001) *The Plant Journal* 27, 581-590) such that upon expression in plants an RNA molecule is formed which can fold back upon itself thus forming a hairpin structure that triggers the specific degradation of homologous RNA.

The vector pKANNIBAL contains an intron positioned downstream of the CaMV 35S promoter and upstream form an octopine synthase polyadenylation signal. At either side of the intron a multiple cloning site is positioned which allows convenient insertion of the left and right arm of DNA corresponding to the RNA interference target in a inverted orientation relative to each other. Upon transcription the intron is removed by splicing and the left and right arm fold back on each other forming the double stranded RNA.

Two cDNA fragments were isolated corresponding to the 5'-end of the gene (588 bp, forward primer: 5'-ACC TCC GAG AAC TCC GTT AAG-3' (SEQ ID NO: 1), reverse primer: 5'-TGC CTG CTT TCT ACC ACT TC-3') (SEQ ID NO: 2) and the middle part of the gene (679 bp, forward primer: 5'-TTC TCA AGT GGC AAG GTG TC-3' (SEQ ID NO: 3); reverse primer: 5'-ATC CCT CTT TGG TGG AGT AG-3') (SEQ ID NO: 4). Restriction enzyme recognition sites were generated at both sides of each fragment which allowed the insertion of the cDNA fragments as an inverted repeat in pKANNIBAL. The left arm for both fragments is engineered as an XhoI-KpnI fragment whereas the right arm for both fragments is engineered as a HindII-XbaI fragment. As a final step the complete hairpin cassettes, containing the both Tetraspore sequences as inverted repeat, are inserted separately into a T-DNA of a binary vector called pART27 which contains the neomycin phosphotransferase II gene as selectable marker for plant transformation. The integrity of the T-DNA was confirmed by sequence analysis.

The resulting binary vectors, denominated pRZ226 for the 5'-fragment and pRZ219 for the 3'-fragment are transferred into *Agrobacterium tumefaciens* using a triparental mating procedure. In case the sequence similarity between a fragment of a cloned candidate target gene and the specific gene that needs to be downregulated by RNA interference is too low, the method described above can be used to make a similar construct containing DNA fragments which are sufficiently homologous to the gene that needs to be downregulated.

Example 5

Transformation of *Arabidopsis Thaliana* with pRZ226 and pRZ219

*Agrobacterium tumefaciens* strain C58 containing the plant transformation vectors pRZ226 and pRZ219 were grown overnight in LB medium containing streptinomycin (100 mg/L) and spectinomycin (300 mg/L) to select for the vectors and rifampicin (40 mg/L) and gentamycin (25 mg/L) to select for the *Agrobacterium tumefaciens* C58 background at 29° C.

In order to produce transgenic plants, the *Arabidopsis* floral dip method was used largely as described by Desfeux et al (2000) *Plant Physiology* 123, 895-904. The bacterial cells were resuspended in floral dip solution (50 g sucrose+500 μl silwett L-77 surfactant per liter milliQ). Bolting plants, containing multiple floral buds, were submerged into the dipping solution containing the *Agrobacterium* cells at an OD between 1.0 and 1.5 during 5-10 seconds with gentle agitation. After inoculation, the plants were contained in a plastic container to keep high humidity under low light conditions for a day and subsequently, seeds were grown on the plants.

Transformants were selected by germinating surface sterilised seeds in 0.1% agarose layered upon half-strength MS plates containing 50 mg/L kanamycin. Kanamycin resistant seedlings were transferred to soil in a greenhouse.

Example 6

Naturally Occurring SDR Event in *Brassica Oleracea*

Hybrids produced on red cabbage (*Brassica oleracea*) carrying Ogura cytoplasmic male sterility (CMS) through a wide cross were screened for the occurrence of diploid plants which were phenotypically nearly identical to the original red cabbage CMS plant and which therefore are the result of in vivo gynogenesis. These plants which can easily be distinguished from true hybrid plants on the basis of their phenotype were indeed identified with low frequency.

Such plants originate through parthenogenesis from reduced gametes which doubled spontaneously or from unreduced gametes. In order to discriminate between these possibilities, the DNA derived from such plant was analysed using AFLP (carried out according to EP-534 858). The analysis demonstrated the presence of a relatively low frequency of heterozygous loci indicating that this plant originated from an unreduced gamete. This example shows that through in vivo gynogenesis in *Brassica oleracea*, plants can be obtained with a relatively low level of heterozygocity which is likely caused by an SDR-like mechanism.

Figure 10:
FIG. 10 shows the AFLP fingerprint of a *Brassica oleracea* plant derived from an ureduced gamete. Grey lines indicates a homozygous marker call from one parent, dark grey from the other. Light grey indicates a hybrid marker locus.

FIG. 10 shows the AFLP fingerprint of a *Brassica oleracea* plant derived from an ureduced gamete. Grey lines indicates a homozygous marker call from one parent, dark grey from the other. Light grey indicates a hybrid marker locus.

Example 7

Near Reverse Breeding in Maize

Incorporation of nucleic acids in the genome of maize are routine procedures known in the art and methods how to achieve this have been described (EP-801134; U.S. Pat. No. 5,489,520; EP-97.114654.3). Using any one of the transformation methods described in these patent applications, nucleic acid sequences were introduced that confer a specific inhibitory effect on a gene or genes which are involved in the second meiotic division, in particular elongate1 (Barell, P J and Grossniklaus, U. (2005) *Plant J.* 43, 309-320) and which as a consequence lead to the occurrence of aberrant meiotic events of the SDR type. The frequency of SDR-events obtained sometimes differs between independent transformants as a consequence of different genomic sites of integration of the transgenic nucleic acid sequences.

In another experiment the frequency of SDR spores was increased by treatment of maize plants with low temperatures or by applying nitrous oxide gas as described by Kato, A and Birchler, J A (2006) *J. Hered.* 1, 39-44.

As a consequence of the activity of the said inhibitory nucleic acids or application of low temperatures or nitrous oxide treatments, numerous microspores respectively macrospores, were produced which are of the SDR-type.

The cell population thus produced was enriched for the presence of SDR-0 microspores by using flow cytometry and fluorescence activated cell sorting based on the fact that SDR microspores are larger in size as compared to normal haploid micropsores.

The microspores or macrospores which were produced as a consequence of an SDR-event contain a diploid set of chromosomes. These diploid microspores or macrospores were the starting material for producing SDR-0 regenerants.

Haploid maize plants have also been obtained following natural and artificial pollination with a haploid inducer. In this case seeds are obtained that contain haploid embryos see fi. Rotarenco V (2002) Production of matroclinous maize haploids following natural and artificial pollination with a haploid inducer. Maize Genetics Cooperation News Letter 76: 16. The mentioned protocols to produce DH maize plants have also be applied to produce SDR-0 maize embryos from SDR-0 cells, of which the formation is induced by the treatments specified in this example. In order to obtain the proper balance between the maternal and paternal genomes in the endosperm of the SDR-0 kernels, use has also been made of a tetraploid inducer line.

In the specific experiment in which transgenesis is applied to induce SDR, transformants that contained a single copy of the transgene were preferred. After obtaining a transgenic line containing a nucleic acid construct that largely inhibits the second meiotic division, this line was used in crosses in order to avoid repetitive transformation events. In that case the frequency of normal pollen containing haploid gametes was low but still sufficient to be used for crossing.

In a further experiment, an inhibitory nucleic acid construct was used which is controlled by a promoter that is chemically inducible by e.g. dexamethasone (Bohner, S. et al (1999) Plant J. 19, 87-95).

Haploids in maize were then routinely obtained from microspores (Pescitelli S and Petolino J (1988) *Plant Cell Reports* 7: 441-444; Coumans M et al., (1989) *Plant Cell Reports* 7: 618-621; Pescitelli S et al., (1989) *Plant Cell*

Reports 7: 673-676; Buter B (1997) In vitro haploid production in maize. In: In Vitro Haploid Production in Higher plants, vol 4, 37-71. Kluwer Academic Publishers. Eds.; S Jain, S Sopory & R Veilleux).

Haploid maize plants were also be obtained following natural and artificial pollination with a haploid inducer (Rotarenco V (2002) *Maize Genetics Cooperation News Letter* 76: 16). In this case seeds were obtained that contain haploid embryos.

The above-mentioned protocols to produce DH maize plants were applied to produce SDR-0 maize plants from SDR-0 cells, of which the formation is induced transgenically or by the other treatments specified in this example.

The SDR-0 maize plants were genetically characterised with respect to the centromeric regions of each chromosome using a molecular marker which is polymorphic for these regions in the original starting plant. For the detection of the polymorphism different technologies, selected from CAPS, dCAPS, Invader, pyrosequencing, taqman were used.

Thus, couples of SDR-0 maize plants were identified which are complementary for all chromosomal pairs with respect to the marker scores of the centromeric regions. Such couples of SDR-0 maize plants were then used to produce doubled haploid plants for each SDR-0 complementary plant. The individual DHs obtained from each complementary SDR-0 plant were crossed pairwise i.e. the two DHs which are used to produce a maize F1 hybrid originate from either one of the complementary SDR-0 events. These crosses were made reciprocally. The F1 hybrids thus produced were evaluated in field trials for agronomic performance in which the starting F1 hybrid was used as a control.

It was found that the agronomic performance of the hybrid obtained through near reverse breeding of the invention is similar to the performance of the original hybrid.

Example 8

Near Reverse Breeding in Cucumber

Gynogenesis is a well established technology for cucumber and is carried out according to the method described in EP 0 374 755. Spontaneous SDR events which occur during gynogenesis when applied according to EP 0 374 755 led to the formation of diploid regenerants which have some residual heterozygocity. These SDR-0 cucumber plants were identified using AFLP analysis carried out according to the method provided in EP 534858.

The SDR-0 cucumber plants thus obtained were genetically characterised with respect to the centromeric regions of each chromosome using molecular markers which are polymorphic for these regions in the original starting plant. For the detection of the polymorphisms, known technologies selected from CAPS, dCAPS, Invader, pyrosequencing, taqman were used. This resulted in the identification of couples of SDR-0 cucumber plants which were complementary for all chromosomal pairs with respect to the marker scores of the centromeric regions. Such couples of SDR-0 cucumber plants were subsequently used to produce DH plants for each SDR-0 complementary plant according to the method described in EP 0 374 755.

Spontaneous occurring SDR events were discarded and only true doubled haploid plants were used in further steps. In case haploid plants were obtained the chromosome number is doubled e.g. by applying colchicine. The chromosome doubling can also occur spontaneously. The individual DH plants obtained from each complementary SDR-0 plant were subsequently crossed pairwise i.e. the two DHs which were used to produce a cucumber F1 hybrid originated from either one of the complementary SDR-0 events. These crosses were made reciprocally. The F1 hybrids thus produced were evaluated in trials for agronomic performance in which the starting F1 hybrid is used as a control.

It was found that the agronomic performance of the hybrid obtained through near reverse breeding of the invention is similar to the performance of the original F1 hybrid.

Various modifications and variations of the described products and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

We claim:

1. A method for producing a homozygous plant from a heterozygous plant, which homozygous plant can be crossed to obtain a hybrid, comprising:
   a) providing a heterozygous starting plant;
   b) inducing the plant to produce second division restitution (SDR)-0 cells originating from second division restitution after meiotic recombination;
   c) regenerating SDR-0 plants from the SDR-0 cells;
   d) selecting for plants produced from cells originating from second division restitution using molecular markers; and
   e) producing the homozygous plant from the SDR-0 plants by doubled haploid techniques, inbreeding, second division restitution, or combinations thereof.

2. The method as claimed in claim 1, wherein SDR frequency is naturally occurring in the starting plant.

3. The method as claimed in claim 1, wherein the SDR-0 cells are produced by a plant showing an increased frequency in second division restitution (SDR) as compared to a frequency of naturally occurring SDR.

4. The method as claimed in claim 1, wherein the plant producing the SDR-0 cells is genetically modified to show an increased frequency in second division restitution (SDR) as compared to a frequency of naturally occurring SDR.

5. The method as claimed in claim 4, wherein the genetic modification is transient.

6. The method as claimed in claim 4, wherein the genetic modification is by stable incorporation into the genome of a genetic element increasing the number of second division restitution events in the plant.

7. The method as claimed in claim 1, wherein the plant producing the SDR-0 cells is subjected to environmental stress to show an increased frequency in second division restitution (SDR) as compared to a frequency of naturally occurring SDR.

8. The method as claimed in claim 7, wherein the environmental stress is selected from temperature stress, nitrogen dioxide, nitrous oxide, and combinations thereof.

9. A method for producing a hybrid comprising crossing a first homozygous plant produced according to claim 1 with a second homozygous plant.

10. The method as claimed in claim 9, wherein the second homozygous plant is at least partially complementary to the first homozygous plant such that the resulting hybrid has at least 50% of the heterozygosity of the starting plant.

11. The method as claimed in claim 10, wherein the resulting hybrid has any percentage between 50 and 100% of the heterozygosity of the starting plant.

12. The method as claimed in claim 9, wherein the second homozygous plant is selected such that the resulting hybrid outperforms the heterozygous starting plant.

13. The method as claimed in claim 9, wherein the second homozygous plant is selected such that only a subset of its chromosomes is complementary to the corresponding chromosomes of the first homozygous plant.

14. The method as claimed in claim 13, wherein the chromosomes which are not complementary to the corresponding chromosomes of the first homozygous plant are identical between the first and second homozygous plants.

15. The method as claimed in claim 1 wherein the selecting is performed on the basis of visual inspection or by means of molecular markers.

16. A method of producing a homozygous plant, or part thereof, comprising producing progeny by self-pollinating the homozygous plant obtained by the method of claim 1.

17. A method of producing a hybrid plant, or part thereof, comprising producing progeny by crossing the hybrid plant obtained by the method of claim 9 with a homozygous plant.

* * * * *